United States Patent [19]

Morimoto et al.

[11] Patent Number: 5,321,171
[45] Date of Patent: Jun. 14, 1994

[54] METHOD FOR PRODUCING METHYL CHLORIDE

[75] Inventors: Takeshi Morimoto; Shinsuke Morikawa; Hirokazu Takagi; Naoki Yoshida, all of Yokohama, Japan

[73] Assignee: Asahi Glass Company Ltd., Tokyo, Japan

[21] Appl. No.: 77,765

[22] Filed: Jun. 18, 1993

[30] Foreign Application Priority Data

Jun. 19, 1992 [JP] Japan .................................. 4-186344
Jun. 30, 1992 [JP] Japan .................................. 4-196560
Mar. 30, 1993 [JP] Japan .................................. 5-095577

[51] Int. Cl.⁵ .............................................. C07C 17/16
[52] U.S. Cl. .................................................... 570/258
[58] Field of Search ......................................... 570/258

[56] References Cited

U.S. PATENT DOCUMENTS 3,872,175  3/1975  Robota et al. .

OTHER PUBLICATIONS

Chemical Abstracts, vol. 102, No. 9, Mar. 4, 1985, AN-78351j, p. 552, JP-A-59 184 139, Oct. 19, 1984.
Chemical Abstracts, vol. 86, No. 25, Jun. 20, 1977, AN-189178d, p. 546, JP-A-7 705 702, Jan. 17, 1977.

*Primary Examiner*—Howard T. Mars
*Attorney, Agent, or Firm*—Oblon, Spivak, McClelland, Maier & Neustadt

[57] ABSTRACT

A method for producing methyl chloride, which comprises reacting methanol and hydrogen chloride in a gas phase in the presence of a catalyst, wherein a zirconium oxide catalyst or a composite catalyst comprising at least two oxides of metals selected from the group consisting of Zr, Ti and Al, is used as the catalyst.

6 Claims, No Drawings

METHOD FOR PRODUCING METHYL CHLORIDE

The present invention relates to a method for producing methyl chloride which comprises reacting methanol and hydrogen chloride in a gas phase in the presence of a novel catalyst.

Methyl chloride is widely recognized to be useful as a starting material for silicone, butyl rubber, methyl cellulose, chloroform, carbon tetrachloride or the like. However, no industrially satisfactory method for its production has not yet been known.

Heretofore, as a method for producing methyl chloride, a method by means of a gas phase chlorination reaction of methane or a method by means of a liquid phase hydrochlorination reaction of methanol using a Friedel Crafts catalyst such as a metal halide as the catalyst, has been known. Further, a method is also known wherein methanol and hydrogen chloride are reacted in a gas phase in the presence of an alumina catalyst (Japanese Examined Patent Publications No. 15733/1982 and No. 30248/1973).

However, the above conventional methods have various drawbacks, respectively.

Namely, the method of the gas phase chlorination of methane requires a large installation, and simultaneously produces methylene chloride, chloroform, carbon tetrachloride, etc. as by-products. Accordingly, separation of such by-products and purification are required. Thus, an extremely complex operation is required, and the reaction temperature is high, whereby a side reaction such as formation of carbon is likely to occur, and selectivity for methyl chloride is very low.

On the other hand, the method of the liquid phase hydrochlorination reaction of methanol has difficulties such that deterioration of the catalyst is remarkable since water is present in the system, conversion of the methanol is low, the reaction rate is low, and selectivity for methyl chloride is low since a side reaction such as formation of dimethyl ether is likely to occur. Thus, such a method is not suitable as a method for industrial application.

Further, the method of reacting methanol and hydrogen chloride in a gas phase in the presence of an alumina catalyst, requires a high temperature reaction to attain a high degree of conversion of methanol and, as such, is disadvantageous from the viewpoint of e.g. the durability of the catalyst or the control of decomposition of methyl chloride.

The object of the present invention is to solve the above described problems and to provide a means to accomplish a high methanol conversion and selectivity for methyl chloride even by a low temperature reaction (for example, at a reaction temperature of from about 200° to 250° C.) in a method for producing methyl chloride by reacting methanol and hydrogen chloride in a gas phase.

The present invention provides anew a method for producing methyl chloride, which comprises reacting methanol and hydrogen chloride in a gas phase in the presence of a catalyst, wherein a zirconium oxide catalyst or a composite catalyst comprising at least two oxides of metals selected from the group consisting of Zr, Ti and Al, is used as the catalyst.

Now, the present invention will be described in detail with reference to the preferred embodiments.

As the zirconium oxide, an oxide of tetravalent zirconium (hereinafter referred to as zirconia) is usually employed, and the specific surface area is preferably at least 10 m$^2$/g, more preferably at least 50 m$^2$/g. The titanium oxide may, for example, be an oxide of bivalent titanium, trivalent titanium or tetravalent titanium, but an oxide of tetravalent titanium (hereinafter referred to as titania) is usually preferably employed. The titania is preferably the one having a specific surface area of at least 10 m$^2$/g, more preferably at least 50 m$^2$/g. As the aluminum oxide, an oxide of trivalent aluminum (hereinafter referred to as alumina) is usually employed, and particularly preferred is γ-alumina. The specific surface area of the alumina is preferably at least 10 m$^2$/g, more preferably at least 50 m$^2$/g.

In the present invention, the zirconium oxide catalyst may be used alone, or a complex oxide catalyst having two or three types of metal oxides selected from the above-mentioned three types of specific metal oxides, may be used. Specifically, a combination of zirconium oxide-titanium oxide, zirconium oxide-aluminum oxide, titanium oxide-aluminum oxide or zirconium oxide-titanium oxide-aluminum oxide) may, for example, be mentioned. The mixing ratio of these three types of specific metal oxides is not particularly limited and can be changed within a wide range. However, if aluminum oxide is too much, the effects of the present invention tend to be hardly observed. Accordingly, it is usually preferred to use aluminum oxide in an amount of not higher than 95 wt %, preferably not higher than 80 wt %.

In the present invention, it is possible to use a catalyst having an oxide of at least one metal selected from the group consisting of zinc, copper, manganese, cobalt, chromium, iron and nickel incorporated to the above-mentioned zirconium oxide catalyst or to the complex oxide catalyst. The starting material for such an additional metal oxide may be in any chemical form. For example, it is possible to employ a nitrate, a hydrochloride, a carbonate, an acetate, a hydroxide, a complex salt or an alkoxide of such a metal element. A solution can be prepared by a preparation method suitable to the chemical form of the starting material. However, it is preferred to employ a nitrate or an acetate as the starting material, since it is thereby possible to secure a good solubility in a solvent, a good dispersibility of the additional metal oxide and a good pyrolytic property during calcination. Such metal salts may be used in combination as a mixture of two or more, if desired.

There is no particular restriction as to the manner of incorporating such an additional metal oxide to the zirconium oxide catalyst or to the complex oxide catalyst, and any method which is commonly used for the preparation of a catalyst, such as an impregnation method, a coprecipitation method or a kneading method, may be employed. Namely, an impregnation method may be employed wherein a solution having a salt of the additional metal dissolved in water or in an organic solvent such as methanol, ethanol or acetone, preferably a solution having such a salt dissolved in water, is impregnated to the zirconium oxide catalyst or to the complex oxide catalyst, followed by drying. Otherwise, a coprecipitation method may be employed wherein salts of metal sources of the above-mentioned specific metal oxides and a metal source of the additional metal oxide are dissolved in water or in an organic solvent such as an alcohol and then co-precipitated with a neutralizing agent such as aqueous ammonia or sodium carbonate, followed by washing, filtration and then drying.

The amount of the additional metal oxide incorporated to or supported on the zirconium oxide catalyst or the complex oxide catalyst is selected within a range of from 1 to 20 wt %. However, an amount of from 3 to 15 wt % is preferred from the viewpoint of the effects.

In the present invention, it is preferred to employ a catalyst prepared by dispersing an oxide of Zn as a first component in an oxide of at least one metal selected from the group consisting of Zr and Ti, or in a complex oxide comprising at least two oxides of metals selected from the group consisting of Zr, Ti and Al, as a second component.

The surface of the first component (ZnO) as the active component dispersed in the specific metal oxide as the second component, will be chlorinated by HCl in the feed gas and thus will serve as active sites. The higher the active component dispersed in the catalyst, the higher the catalytic activities. Catalysts containing the first component and the second component all show a high degree of conversion of feed material and selectivity for methyl chloride at the initial stage, but some catalysts having strong surface acidity exhibit a tendency such that the catalytic activities decrease with time. As a result of the analysis, it has been found that coke precipitates due to condensation or thermal decomposition of the feed material methanol or the product by the action of the strongly acidic sites of the catalyst, and it is believed that due to the precipitation of coke, clogging of pores of the catalyst and a decrease of the surface area result, thus leading to a deterioration of the catalytic activities.

The surface acidity of the catalyst can be measured by an ammonia TPD method (a temperature programmed desorption method). The ammonia TPD method is a method wherein ammonia is chemically adsorbed to the acid sites of the catalyst at a predetermined temperature, and then the temperature is raised, whereupon the amount of desorbed ammonia is measured, and from the peak temperature for desorption of ammonia, the acidity is measured. The stronger the surface acidity of the catalyst, the more strongly ammonia is chemically adsorbed to the acid sites of the catalyst and the higher the peak temperature for the desorption of ammonia. In the measuring operation by this method, 150 mg of the catalyst is first heated at 500° C. for one hour in a He stream of 50 cm³/min for pretreatment. Then, 4% NH₃/He is passed therethrough at 100° C. at a rate of 50 cm³/min for one hour to adsorb ammonia on the catalyst. Then, He is passed therethrough at the same temperature at a rate of 50 cm³/min for one hour to remove ammonia physically adsorbed on the catalyst. Then, the temperature is raised at a rate of 10° C./min in a He stream of 50 cm³/min to desorb the ammonia chemically adsorbed to the acid sites, whereupon the liberated amount is measured by TCD (a thermal conductivity detector).

By this method, the acidities of various catalysts were measured, whereby it has been confirmed that with catalysts having relatively weak acidities whereby the peak temperature for desorption of ammonia by the above-mentioned ammonia TPD method is not higher than 350° C., preferably not higher than 300° C., no substantial deterioration occurs even when a continuous operation is conducted for at least 2,000 hours, and the durability has been substantially improved. The peak temperature for desorption of ammonia is usually preferably at least 100° C.

The starting material for the component (ZnO) as the active component may be in any chemical form. For example, it is possible to employ a nitrate, a hydrochloride, an acetate, a hydroxide or a complex salt. A solution is prepared by a preparation method suitable for the chemical form of the starting material. However, it is usually preferred to employ a nitrate or an acetate as the starting material, since it is thereby possible to secure a good solubility in a solvent, a good dispersibility on a support and a good pyrolytic property during calcination. Such a metal salt is dissolved in water or in an organic solvent such as methanol, ethanol or acetone, preferably in water, and the solution thereby obtained is impregnated to the second component (specific metal oxides) as the support, followed by drying to obtain a catalyst. Catalysts prepared by a coprecipitation method show even higher activities than those obtained by the impregnation method, since the first component as the active component can thereby be highly and stably dispersed in the catalyst.

Also in the coprecipitation method, the starting material salts for the first component and the second component may be in any chemical forms. For example, nitrates, hydrochlorides, carbonates, acetates, hydroxides, complex salts or alkoxides of these metal elements may be employed. A starting material salt solution is prepared by a preparation method suitable to the chemical forms of the starting materials. However, it is particularly preferred to use nitrates or acetates as the starting materials, since it is thereby possible to secure good solubilities in a solvent, good dispersibilities of the catalyst components and good pyrolytic properties during calcination. Salts of the specific metals may be used in combination as a mixture of two or more of them, if desired.

Such metal salts are dissolved in water or in an organic solvent such as an alcohol, preferably in water, and if necessary, an acid or an alkali is added to adjust the pH, to obtain a starting material salt solution having metal elements adjusted to a predetermined compositional ratio. This starting material salt solution and a precipitating agent such as aqueous ammonia or sodium carbonate are simultaneously gradually dropwise added under stirring to a buffer solution employing e.g. ammonium nitrate, to form a co-precipitated gel. The conditions for formation of the coprecipitated gel, such as the pH, the temperature, the concentration of the starting material salt solution and the rate of its addition are selected to be suitable for the chemical forms of the starting material salts. Further, by controlling these conditions, it is possible to obtain a catalyst having a desired surface area, particle size and pore size distribution. The gel thus obtained may be aged, as the case requires, followed by washing with water and then drying. Incorporation of a catalyst component which does not form precipitates by the coprecipitation operation, can be conducted by e.g. an impregnation method or a kneading method in a suitable form such as a powder form after drying the coprecipitated gel.

The amount of incorporation of the first component in the catalyst thus prepared by the above method, is selected within a range of from 0.01 to 20 wt %. However, in the impregnation method, the amount is preferably from 3 to 15 wt %, and in the coprecipitation method, the amount is preferably from 0.1 to 15 wt %, from the viewpoint of economy and effects.

The catalyst of the present invention may further contain other additive components in addition to the first component and the second component. For example, as an acidity suppressing component, an oxide of at least one metal selected from the group consisting of alkali metals, alkaline earth metals and rare earth metals, may be added. Such an oxide may, for example, be an oxide of e.g. magnesium, sodium, potassium, calcium, cerium, lithium or yttrium. The amount of such acidity-suppressing component to be incorporated or supported is preferably from 0.1 to 5 wt %, more preferably from 0.5 to 3 wt %, from the viewpoint of effects.

The catalyst to be used in the present invention may be subjected to calcination, if desired, after drying. As the calcination conditions, a temperature of from 300° to 700° C., preferably from 400° to 600° C. and a time of from 1 to 20 hours, preferably from 2 to 10 hours, may be employed. However, such conditions are not particularly limited. The shape or the like of the catalyst may be the one commonly known in the art. For example, the catalyst may be pelletized and used in various shapes.

In the present invention, it is possible to produce methyl chloride at a low cost by using by-product hydrogen chloride containing hydrogen fluoride or the like produced as a by-product by the fluorination reaction of a compound instead of expensive synthesized hydrogen chloride. Accordingly, the present invention provides an effective and efficient method of utilizing by-product hydrogen chloride containing hydrogen fluoride, which used to have a very limited use and which used to require a substantial cost for fluorine-removing treatment.

The concentration of hydrogen fluoride in the hydrogen chloride is preferably less than 10% from the viewpoint of the safety and the durability of the apparatus.

The by-product hydrogen chloride containing hydrogen fluoride may, for example, be hydrogen chloride produced in a large amount as a by-product during the production of a fluorinated hydrocarbon, or a fluorinated and chlorinated hydrocarbon, by fluorinating a chlorinated hydrocarbon. Such a by-product hydrogen chloride usually contains from 10 ppm to a few % of hydrogen fluoride.

The reaction system, the reaction apparatus, the reaction conditions, etc. are not particularly limited so long as the reaction can be conducted in a gas phase by means of the catalyst. For example, a fixed bed system or a fluidized bed system can usually be employed. In a case where methanol and hydrogen chloride are reacted in a gas phase by using the above described catalyst, the reaction can be conducted under atmospheric pressure or under elevated pressure (at a level of from 2 to 5 atm). On the other hand, the reaction temperature may be at least the temperature (108° C.) at which hydrochloric acid undergoes condensation. However, the reaction is preferably conducted at a temperature of at least 120° C. from the viewpoint of the reactivity and the selectivity. Otherwise, the reaction rate tends to be slow, whereby the yield will be low. Further, the amount of dimethyl ether to be produced as a by-product, will increase. Further, a non-reacted substance and water produced as a by-product by the reaction of methanol and hydrogen chloride, tend to remain in the reaction system, and they tend to adversely affect the catalyst, or the reaction apparatus will substantially be corroded.

Further, with respect to the molar ratio of hydrogen chloride to methanol ($HCl/CH_3OH$ ratio), either one may be in excess. However, if methanol is in large excess, the conversion of hydrogen chloride tends to be low. Therefore, the $HCl/CH_3OH$ molar ratio is preferably from 1.0 to 1.5 for an industrial operation. Further, the space velocity (SV) in the reactor is preferably from 200 to 10,000 $h^{-1}$, preferably from 300 to 3,000 $h^{-1}$. The reaction product is usually separated from the non-reacted substance and collected by a conventional method.

The catalyst to be used in the present invention has high catalytic activities as compared with a conventional catalyst such as alumina, whereby the reaction can be conducted at a lower temperature, and there will be merits such that the durability of the catalyst increases, and decomposition of methyl chloride will decrease. Further, the catalyst can be used in the form of spherical particles, whereby the pressure difference between before and after the catalyst bed during the continuous operation, can be small. Accordingly, the power required to supply the gas to the catalytic bed can be saved.

Now, the present invention will be described in further detail with reference to Examples. However, it should be understood that the present invention is by no means restricted by such specific Examples.

EXAMPLE 1

Commercially available zirconia powder (specific surface area: 100 $m^2/g$) was calcined in an electric furnace at 500° C. for three hours, and the calcined product was press-molded under a gauge pressure of 120 $kg/cm^2$, followed by pulverization and classification with sieves to obtain a catalyst having a particle size of from 10 to 20 mesh. 6 ml of this catalyst was packed into a glass reactor having an inner diameter of 14 mm and heated to a predetermined temperature, whereupon a reaction was conducted by supplying methanol and hydrogen chloride in a molar ratio of $HCl/CH_3OH=1.4$ at a space velocity $SV=2,200$ $h^{-1}$. The results are shown in Table 1.

TABLE 1

| Reaction temperature (°C.) | Conversion of methanol (mol %) | Selectivity for methyl chloride (mol %) |
| --- | --- | --- |
| 200 | 10.1 | 93.5 |
| 250 | 15.8 | 94.3 |
| 300 | 57.2 | 97.5 |
| 300 | 84.2 | 98.5 |

EXAMPLE 2

Commercially available zirconia powder (specific surface area: 80 $m^2/g$) was immersed into an aqueous zinc nitrate solution and then dried at 120° C. for 10 hours. Then, it was calcined at 500° C. for 4 hours so that zinc oxide was supported thereon in an amount of 10 wt %. This material was press-molded under a gauge pressure of 150 $kg/cm^2$, followed by pulverization and classification with sieves to obtain a test catalyst having a particle size of from 7 to 15 mesh. 6 ml of this catalyst was packed into a glass reactor having an inner diameter of 14 mm and heated to a predetermined temperature. A reaction was conducted by supplying methanol and hydrogen chloride thereto in a molar ratio of HCl/CH$_3$OH = 1.3 at a space velocity SV = 2,500 h$^{-1}$. The results are shown in Table 2.

TABLE 2

| Reaction temperature (°C.) | Conversion of methanol (mol %) | Selectivity for methyl chloride (mol %) |
|---|---|---|
| 200 | 98.5 | 99.8 |
| 250 | 100.0 | 100.0 |
| 300 | 100.0 | 100.0 |
| 350 | 100.0 | 100.0 |

EXAMPLE 3

Commercially available zirconia powder (specific surface area: 80 m$^2$/g) was immersed into an aqueous chromium acetate solution and then dried at 120° C. for 6 hours. Then, the dried product was calcined at 450° C. for 4 hours so that chromium oxide was supported thereon in an amount of 9 wt %. The product was press-molded under a gauge pressure of 130 kg/cm$^2$, followed by pulverization and classification with sieves to obtain a test catalyst having a particle size of from 10 to 20 mesh. 6 ml of this catalyst was packed into a glass reactor having an inner diameter of 14 mm and heated to a predetermined temperature. A reaction was conducted by supplying methanol and hydrogen chloride in a molar ratio of HCl/CH$_3$OH = 1.4 at a space velocity SV = 2,200 h$^{-1}$. The results are shown in Table 3.

TABLE 3

| Reaction temperature (°C.) | Conversion of methanol (mol %) | Selectivity for methyl chloride (mol %) |
|---|---|---|
| 200 | 95.3 | 99.3 |
| 250 | 98.2 | 99.7 |
| 300 | 99.9 | 99.9 |
| 350 | 100.0 | 99.9 |

EXAMPLE 4

Commercially available zirconia powder (specific surface area: 100 m$^2$/g) was immersed in an aqueous copper acetate solution. The powder was dried at 110° C. for 9 hours, and then calcined at 500° C. for 3 hours so that copper oxide was supported thereon in an amount of 11 wt %. The product was press-molded under a gauge pressure of 140 kg/cm$^2$, followed by pulverization and classification with sieves to obtain a test catalyst having a particle size of from 7 to 15 mesh. 6 ml of this catalyst was packed into a glass reactor having an inner diameter of 14 mm and heated to a predetermined temperature. Then, a reaction was conducted by supplying thereto methanol and hydrogen chloride in a molar ratio of HCl/CH$_3$OH = 1.3 at a space velocity SV = 2,500 h$^{-1}$. The results are shown in Table 4.

TABLE 4

| Reaction temperature (°C.) | Conversion of methanol (mol %) | Selectivity for methyl chloride (mol %) |
|---|---|---|
| 200 | 15.3 | 98.0 |
| 250 | 90.3 | 99.8 |
| 300 | 99.2 | 99.9 |
| 350 | 100.0 | 99.8 |

EXAMPLE 5

Commercially available zirconia powder (specific surface area: 100 m$^2$/g) was immersed in an aqueous manganese nitrate solution, then dried at 100° C. for 12 hours and then calcined at 550° C. for 4 hours so that manganese oxide was supported thereon in an amount of 9 wt %. The product was press-molded under a gauge pressure of 130 kg/cm$^2$, followed by pulverization and classification with sieves to obtain a test catalyst having a particle size of from 10 to 20 mesh. 6 ml of this catalyst was packed into a glass reactor having an inner diameter of 14 mm and heated to a predetermined temperature, and then a reaction was conducted by supplying hydrogen chloride and methanol in a molar ratio of HCl/CH$_3$OH = 1.4 at a space velocity SV = 2,300 h$^{-1}$. The results are shown in Table 5.

TABLE 5

| Reaction temperature (°C.) | Conversion of methanol (mol %) | Selectivity for methyl chloride (mol %) |
|---|---|---|
| 200 | 20.3 | 98.0 |
| 250 | 98.1 | 99.6 |
| 300 | 100.0 | 100.0 |
| 350 | 100.0 | 99.9 |

EXAMPLE 6

Commercially available zirconia powder (specific surface area: 80 m$^2$/g) was immersed in an aqueous cobalt nitrate solution and then dried at 110° C. for 8 hours. Then, it was calcined at 500° C. for 4 hours so that cobalt oxide was supported thereon in an amount of 9 wt %. The product was press-molded under a gauge pressure of 120 kg/cm$^2$, followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride in a molar ratio of HCl/CH$_3$OH = 1.3 at a space velocity SV = 2,500 h$^{-1}$. The results are shown in Table 6.

TABLE 6

| Reaction temperature (°C.) | Conversion of methanol (mol %) | Selectivity for methyl chloride (mol %) |
|---|---|---|
| 200 | 18.2 | 98.0 |
| 250 | 95.8 | 99.2 |
| 300 | 99.5 | 99.4 |
| 350 | 100.0 | 100.0 |

EXAMPLE 7

Commercially available zirconia powder (specific surface area: 100 m$^2$/g) was immersed in an aqueous iron nitrate solution. This powder was dried at 110° C. for 12 hours and then calcined at 600° C. for two hours so that iron oxide was supported thereon in an amount of 10 wt %. The product was press-molded under a gauge pressure of 150 kg/cm$^2$, followed by pulverization and classification with sieves to obtain a test catalyst having a particle size of from 7 to 15 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH = 1.5 at a space velocity SV = 2,500 h$^{-1}$. The results are shown in Table 7.

TABLE 7

| Reaction temperature (°C.) | Conversion of methanol (mol %) | Selectivity for methyl chloride (mol %) |
| --- | --- | --- |
| 200 | 70.2 | 99.0 |
| 250 | 98.3 | 99.7 |
| 300 | 100.0 | 99.9 |
| 350 | 100.0 | 99.9 |

EXAMPLE 8

Commercially available zirconia powder (specific surface area: 100 m$^2$/g) was immersed in an aqueous nickel acetate solution. The powder was dried at 120° C. for 6 hours and then calcined at 500° C. for 3 hours so that nickel oxide was supported thereon in an amount of 11 wt %. The product was press-molded under a gauge pressure of 120 kg/cm$^2$, followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.4 at a space velocity SV=2,300 h$^{-1}$. The results are shown in Table 8.

TABLE 8

| Reaction temperature (°C.) | Conversion of methanol (mol %) | Selectivity for methyl chloride (mol %) |
| --- | --- | --- |
| 200 | 85.3 | 98.9 |
| 250 | 99.9 | 99.8 |
| 300 | 100.0 | 100.0 |
| 350 | 100.0 | 100.0 |

EXAMPLE 9

Using zinc nitrate as the zinc source and zirconium oxynitrate as the zirconium source, a mixed aqueous solution was prepared so that the molar ratio of Zn/Zr=0.1/1. This mixed aqueous solution and 10% aqueous ammonia was gradually dropwise added to water under stirring to maintain pH=8, to form a co-precipitated gel. The gel was left to stand still for one day and then subjected to washing with water and filtration, and it was dried at 110° C. for 20 hours. The product was further pulverized and calcined at 500° C. for 10 hours to obtain a complex oxide catalyst of ZnO—ZrO$_2$. This complex oxide catalyst had a ZnO content of 6.2 wt % and a specific surface area of 95 m$^2$/g. Then, this catalyst was press-molded under a gauge pressure of 150 kg/cm$^2$, followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.5 at a space velocity SV=2,000 h$^{-1}$. The results are shown in Table 9.

TABLE 9

| Reaction temperature (°C.) | Conversion of methanol (mol %) | Selectivity for methyl chloride (mol %) |
| --- | --- | --- |
| 200 | 99.8 | 99.9 |
| 250 | 100.0 | 100.0 |
| 300 | 100.0 | 100.0 |
| 350 | 100.0 | 100.0 |

EXAMPLE 10

Using zinc chloride as the zinc source and zirconium oxychloride as the zirconium source, a mixed aqueous solution was prepared so that the molar ratio of Zn/Zr=0.01/1. This mixed aqueous solution and 10% aqueous ammonia were gradually dropwise added to water under stirring to maintain pH=8, to form a co-precipitated gel. The gel was left to stand still for one day and then subjected to washing with water and filtration, and it was dried at 120° C. for 15 hours. The product was further pulverized and calcined at 550° C. for 8 hours to obtain a complex oxide catalyst of ZnO—ZrO$_2$. This complex oxide catalyst had a ZnO content of 0.6 wt % and a specific surface area of 90 m$^2$/g. Then, this catalyst was press-molded under a gauge pressure of 140 kg/cm$^2$, followed by pulverization and classification with sieves to obtain a test catalyst having a particle size of from 7 to 15 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.5 at a space velocity SV=1,800 h$^{-1}$. The results are shown in Table 10.

TABLE 10

| Reaction temperature (°C.) | Conversion of methanol (mol %) | Selectivity for methyl chloride (mol %) |
| --- | --- | --- |
| 200 | 99.8 | 99.9 |
| 250 | 100.0 | 100.0 |
| 300 | 100.0 | 100.0 |
| 350 | 100.0 | 100.0 |

EXAMPLE 11

Using chromium nitrate as the chromium source and zirconium oxychloride as the zirconium source, a mixed aqueous solution was prepared so that the molar ratio of Cr/Zr=0.1/1. This mixed aqueous solution and 10% aqueous ammonia were gradually dropwise added to water under stirring to maintain pH=8, to form a co-precipitated gel. The gel was left to stand still for one day and then subjected to washing with water and filtration, and it was dried at 100° C. for 20 hours. The product was further pulverized and calcined at 500° C. for 8 hours to obtain a complex oxide catalyst of Cr$_2$O$_3$—ZrO$_2$. This complex oxide catalyst had a Cr$_2$O$_3$ content of 11.0 wt % and a specific surface area of 85 m$^2$/g. Then, this catalyst was press-molded under a gauge pressure of 150 kg/cm$^2$, followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.6 at a space velocity SV=2,200 h$^{-1}$. The results are shown in Table 11.

TABLE 11

| Reaction temperature (°C.) | Conversion of methanol (mol %) | Selectivity for methyl chloride (mol %) |
| --- | --- | --- |
| 200 | 95.5 | 99.5 |
| 250 | 98.5 | 99.7 |
| 300 | 100.0 | 99.9 |
| 350 | 100.0 | 99.9 |

COMPARATIVE EXAMPLE 1

Commercially available γ-alumina powder (specific surface area: 140 m²/g) was calcined at 500° C. for 4 hours in an electric furnace. The powder was then press-molded under a gauge pressure of 120 kg/cm², followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of $HCl/CH_3OH=1.3$ at a space velocity $SV=2,000$ $h^{-1}$. The results are shown in Table 12.

TABLE 12

| Reaction temperature (°C.) | Conversion of methanol (mol %) | Selectivity for methyl chloride (mol %) |
| --- | --- | --- |
| 200 | 15.8 | 98.3 |
| 250 | 77.5 | 99.1 |
| 300 | 96.3 | 99.8 |
| 350 | 99.8 | 99.8 |

EXAMPLE 12

Using zirconium oxynitrate as the zirconium source and aluminum nitrate as the aluminum source, a mixed aqueous solution was prepared so that the molar ratio of Zr/Al=2. This mixed aqueous solution and 10% aqueous ammonia were gradually dropwise added to water under stirring to maintain pH=8, to form a coprecipitated gel. The gel was left to stand still for one day and then subjected to washing with water and filtration, and it was dried at 110° C. for 20 hours. The product was further pulverized and then calcined at 500° C. for 6 hours to obtain a complex oxide catalyst of $ZrO_2$—$Al_2O_3$. This complex oxide catalyst had a specific surface area of 95 m²/g. This $ZrO_2$—$Al_2O_3$ complex oxide catalyst was immersed in an aqueous zinc acetate solution and then dried at 100° C. for 15 hours. Then, it was calcined at calcined at 550° C. for 3 hours so that zinc oxide was supported thereon in an amount of 11 wt %. Then, this product was press-molded under a gauge pressure of 130 kg/cm², followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of $HCl/CH_3OH=1.5$ at a space velocity $SV=1,600$ $h^{-1}$. The results are shown in Table 13.

TABLE 13

| | Reaction temperature (°C.) | Conversion of methanol (mol %) | Selectivity for methyl chloride (mol %) |
| --- | --- | --- | --- |
| Initial | 200 | 98.7 | 99.9 |
| activities | 250 | 100.0 | 100.0 |
| | 300 | 100.0 | 100.0 |
| | 350 | 100.0 | 100.0 |
| After 2,000 hrs | 200 | 98.8 | 99.8 |

EXAMPLE 13

Using zirconium oxychloride as the zirconium source and titanium isopropoxide as the titanium source, a mixed aqueous solution was prepared so that the molar ratio of Zr/Ti=1.5. This solution and 10% aqueous ammonia were gradually dropwise added to water under stirring to maintain pH=7, to form a coprecipitated gel. This gel was left to stand still for one day and then subjected to washing with water and filtration, and it was dried at 100° C. for 20 hours. The product was further pulverized and calcined at 550° C. for 5 hours to obtain a complex oxide catalyst of $ZrO_2$—$TiO_2$. The obtained $ZrO_2$ complex oxide catalyst had a specific surface area of 96 m²/g. This complex oxide catalyst was immersed in an aqueous zinc nitrate solution and then dried at 110° C. for 12 hours. Then, it was calcined at 500° C. for 4 hours so that zinc oxide was supported thereon in an amount of 10 wt %. Then, the product was press-molded under a gauge pressure of 140 kg/cm², followed by pulverization and classification with sieves to obtain a test catalyst having a particle size of from 7 to 15 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of $HCl/CH_3OH=1.4$ at a space velocity $SV=2,300$ $h^{-1}$. The results are shown in Table 14.

TABLE 14

| | Reaction temperature (°C.) | Conversion of methanol (mol %) | Selectivity for methyl chloride (mol %) |
| --- | --- | --- | --- |
| Initial | 200 | 98.9 | 99.9 |
| activities | 250 | 100.0 | 100.0 |
| | 300 | 100.0 | 100.0 |
| | 350 | 100.0 | 100.0 |
| After 2,000 hrs | 200 | 98.9 | 99.8 |

EXAMPLE 14

Using titanium chloride as the titanium source and aluminum nitrate as the aluminum source, a mixed aqueous solution was prepared so that the molar ratio of Al/Ti=1 and adjusted to pH=0.9 with hydrochloric acid. This solution and 10% aqueous ammonia were gradually dropwise added to water under stirring to adjust pH=8, to form a coprecipitated gel. The gel was left to stand still for one day and then subjected to washing with water and filtration, and it was dried at 100° C. for 20 hours. The product was further pulverized and then calcined at 500° C. for 6 hours to obtain a complex oxide catalyst of $Al_2O_3$—$TiO_2$. The obtained complex oxide catalyst had a specific surface area of 85 m²/g. The complex oxide catalyst was immersed in an aqueous zinc acetate solution and then dried at 110° C. for 10 hours. Then, it was calcined at 500° C. for 3 hours so that zinc oxide was supported thereon in an amount of 9 wt %. Then, the product was press-molded under a gauge pressure of 130 kg/cm², followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of $HCl/CH_3OH=1.5$ at a space velocity $SV=2,100$ $h^{-1}$. The results are shown in Table 15.

TABLE 15

| | Reaction temperature (°C.) | Conversion of methanol (mol %) | Selectivity for methyl chloride (mol %) |
|---|---|---|---|
| Initial activities | 200 | 98.8 | 99.8 |
| | 250 | 100.0 | 100.0 |
| | 300 | 100.0 | 100.0 |
| | 350 | 100.0 | 100.0 |
| After 1,000 hrs | 200 | 98.7 | 99.7 |

EXAMPLE 15

Using zinc nitrate as the zinc source, zirconium oxynitrate as the zirconium source and aluminum nitrate as the aluminum source, a mixed aqueous solution was prepared so that the molar ratio of $Zn/Zr/Al=0.3/1/1$. This solution and 10% aqueous ammonia were gradually dropwise added to water under stirring to maintain pH=8, to form a coprecipitated gel. The gel was left to stand still for one day and then subjected to washing with water and filtration, and then it was dried at 110° C. for 20 hours. The product was further pulverized and then calcined at 550° C. for 6 hours to obtain a complex oxide catalyst of $ZnO-ZrO_2-Al_2O_3$. The complex oxide catalyst had a specific surface area of 62 m²/g. Then, this catalyst was press-molded under a gauge pressure of 140 kg/cm², followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of $HCl/CH_3OH=1.6$ at a space velocity $SV=2,300$ $h^{-1}$. The results are shown in Table 16.

TABLE 16

| | Reaction temperature (°C.) | Conversion of methanol (mol %) | Selectivity for methyl chloride (mol %) |
|---|---|---|---|
| Initial activities | 200 | 98.0 | 99.9 |
| | 250 | 100.0 | 100.0 |
| | 300 | 100.0 | 100.0 |
| | 350 | 100.0 | 100.0 |
| After 1,000 hrs | 200 | 99.1 | 99.9 |

EXAMPLE 16

Using zinc acetate as the zinc source, zirconium oxychloride as the zirconium source and titanium isopropoxide as the titanium source, a mixed aqueous solution was prepared so that the molar ratio of $Zn/Zr/Ti=0.25/1/1$ and adjusted to pH=1 with nitric acid. This solution and 10% aqueous ammonia were gradually dropwise added to water under stirring to maintain pH=8, to form a coprecipitated gel. The gel was left to stand still for one day and then subjected to washing with water and filtration, and then it was dried at 100° C. for 24 hours. The product was further pulverized and then calcined at 500° C. for 6 hours to obtain a complex oxide catalyst of $ZnO-ZrO_2-TiO_2$. This complex oxide catalyst had a specific surface area of 70 m²/g. Then, this catalyst was press-molded under a gauge pressure of 120 kg/cm², followed by pulverization and classification with sieves to obtain a test catalyst having a particle size of from 7 to 15 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of $HCl/CH_3OH=1.4$ at a space velocity $SV=2,300$ $h^{-1}$. The results are shown in Table 17.

TABLE 17

| | Reaction temperature (°C.) | Conversion of methanol (mol %) | Selectivity for methyl chloride (mol %) |
|---|---|---|---|
| Initial activities | 200 | 99.1 | 99.9 |
| | 250 | 100.0 | 100.0 |
| | 300 | 100.0 | 100.0 |
| | 350 | 100.0 | 100.0 |
| After 1,000 hrs | 200 | 99.2 | 99.9 |

EXAMPLE 17

Using zirconium oxychloride as the zirconium source and aluminum nitrate as the aluminum source, a mixed aqueous solution was prepared so that the molar ratio of $Zr/Al=1$. This solution and 10% aqueous ammonia were gradually dropwise added to water under stirring to maintain pH=8, to form a coprecipitated gel. The gel was left to stand still for one day and then subjected to washing with water and filtration, and then it was dried at 110° C. for 15 hours. The product was pulverized and then calcined at 500° C. for 6 hours to obtain a complex oxide catalyst of $Al_2O_3-ZrO_2$. This catalyst had a specific surface area of 95 m²/g. Then, the catalyst was press-molded under a gauge pressure of 130 kg/cm², followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of $HCl/CH_3OH=1.5$ at a space velocity $SV=2,000$ $h^{-1}$. The results are shown in Table 18.

TABLE 18

| Reaction temperature (°C.) | Conversion of methanol (mol %) | Selectivity for methyl chloride (mol %) |
|---|---|---|
| 200 | 75.3 | 99.0 |
| 250 | 77.5 | 99.9 |
| 300 | 98.8 | 100.0 |
| 350 | 100.0 | 100.0 |

EXAMPLE 18

Using zirconium oxychloride as the zirconium source and titanium isopropoxide as the titanium source, a mixed aqueous solution was prepared so that the molar ratio of Zr/Ti=1 and adjusted to pH=1 with nitric acid. This solution and 10% aqueous ammonia were gradually dropwise added to water under stirring to maintain pH=8, to form a coprecipitated gel. The gel was left to stand still for one day and then subjected to washing with water and filtration, and then it was dried at 100° C. for 20 hours. The product was pulverized and then calcined at 500° C. for 5 hours to obtain a complex oxide catalyst of $TiO_2$—$ZrO_2$. The obtained catalyst had a specific surface area of 96 m$^2$/g. Then, the catalyst was press-molded under a gauge pressure of 140 kg/cm$^2$, followed by pulverization and classification with sieves to obtain a test catalyst having a particle size of from 7 to 15 mesh. 6 ml of this catalyst was packed into a glass reactor having an inner diameter of 14 mm and heated to a predetermined temperature. Then, a reaction was conducted by supplying methanol and hydrogen chloride thereto in a molar ratio of $HCl/CH_3OH=1.4$ at a space velocity $SV=2,300$ h$^{-1}$. The results are shown in Table 19.

TABLE 19

| Reaction temperature (°C.) | Conversion of methanol (mol %) | Selectivity for methyl chloride (mol %) |
|---|---|---|
| 200 | 20.5 | 98.1 |
| 250 | 95.5 | 99.8 |
| 300 | 97.4 | 100.0 |
| 350 | 100.0 | 100.0 |

EXAMPLE 19

A complex oxide catalyst of $Al_2O_3$—$ZrO_2$ prepared and calcined in the same manner as in Example 6, was immersed in an aqueous zinc acetate solution and then dried at 120° C. for 8 hours. Then, it was calcined at 500° C. for three hours so that zinc oxide was supported thereon in an amount of 10 wt %. The product was press-molded under a gauge pressure of 150 kg/cm$^2$, followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride in a molar ratio of $HCl/CH_3OH=1.5$ at a space velocity $SV=2,400$ h$^{-1}$. The results are shown in Table 20.

TABLE 20

| Reaction temperature (°C.) | Conversion of methanol (mol %) | Selectivity for methyl chloride (mol %) |
|---|---|---|
| 200 | 99.1 | 99.7 |
| 250 | 100.0 | 100.0 |
| 300 | 100.0 | 100.0 |
| 350 | 100.0 | 100.0 |

EXAMPLE 20

A complex oxide catalyst of $TiO_2$—$ZrO_2$ prepared and calcined in the same manner as in Example 7, was immersed in an aqueous zinc nitrate solution and then dried at 110° C. for 10 hours. Then, it was calcined at 500° C. for 3 hours so that zinc oxide was supported thereon in an amount of 10 wt %. The product was press-molded under a gauge pressure of 140 kg/cm$^2$, followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride in a molar ratio of $HCl/CH_3OH=1.3$ at a space velocity $SV=2,000$ h$^{-1}$. The results are shown in Table 21.

TABLE 21

| Reaction temperature (°C.) | Conversion of methanol (mol %) | Selectivity for methyl chloride (mol %) |
|---|---|---|
| 200 | 98.8 | 99.8 |
| 250 | 100.0 | 100.0 |
| 300 | 100.0 | 100.0 |
| 350 | 100.0 | 100.0 |

COMPARATIVE EXAMPLE 2

Commercially available $\gamma$-$Al_2O_3$ powder (specific surface area: 140 m$^2$/g) was calcined at 500° C. for 4 hours in an electric furnace, and the product was press-molded under a gauge pressure of 150 kg/cm$^2$, followed by pulverization and classification with sieves to obtain a test catalyst having a particle size of from 10 to 20 mesh. 6 ml of this catalyst was packed into a glass reactor having an inner diameter of 14 mm and heated to a predetermined temperature. Then, a reaction was conducted by supplying methanol and hydrogen chloride in a molar ratio of $HCl/CH_3OH=1.4$ at a space velocity $SV=2,000$ h$^{-1}$. The results are shown in Table 22.

TABLE 22

| | Reaction temperature (°C.) | Conversion of methanol (mol %) | Selectivity for methyl chloride (mol %) |
|---|---|---|---|
| Initial activities | 200 | 15.8 | 98.3 |
| | 250 | 77.5 | 99.1 |
| | 300 | 96.3 | 99.8 |
| | 350 | 99.8 | 99.9 |
| After 200 hrs | 200 | 10.3 | 97.5 |

EXAMPLES 21 to 26

Various test catalysts as shown in the following Table 23 was prepared in the same manner as in Example 12. In the column for "Test catalyst" in Table 11, metal species of each complex oxide catalyst and their molar ratio, and the type of the additional metal oxide are indicated. The amount of the additional metal oxide supported, was 10 wt %. 6 ml of such a test catalyst was packed into a glass reactor having an inner diameter of 14 mm and heated to a predetermined temperature. Then, a reaction was conducted by supplying methanol and hydrogen chloride in a molar ratio of $HCl/CH_3OH=1.3$ at a space velocity $SV=2,000$ h$^{-1}$. The results are shown in Table 23. The reaction results after 500 hours in Table 23 are the results of the reaction conducted at a temperature of 200° C.

TABLE 23

| Exam- No. | Test catalyst Metal molar ratio | Kind of additives | Reaction result (mol %) (Upper column: CH₃OH conversion, Lower column: CH₃Cl selectivity) | | | | |
|---|---|---|---|---|---|---|---|
| | | | 200° C. | 250° C. | 300° C. | 350° C. | After 500 hrs |
| 21 | Zr/Ti = 2 | Copper oxide | 17.2 98.1 | 85.5 99.0 | 99.0 99.7 | 100.0 99.9 | 20.2 98.2 |
| 22 | Zr/Ti = 1 | Manganese oxide | 25.2 98.2 | 98.5 99.7 | 100.0 100.0 | 100.0 99.9 | 26.3 98.3 |
| 23 | Ti/Al = 1 | Cobalt oxide | 23.8 98.1 | 96.2 99.4 | 99.7 99.8 | 100.0 100.0 | 23.5 97.9 |
| 24 | Ti/Al = 2 | Chromium oxide | 96.0 99.4 | 98.5 99.8 | 100.0 100.0 | 100.0 100.0 | 95.9 99.4 |
| 25 | Al/Zr = 1 | Iron oxide | 74.8 99.0 | 98.5 99.8 | 100.0 99.9 | 100.0 99.9 | 75.1 99.1 |
| 26 | Al/Zr = 2 | Nickel oxide | 88.7 99.1 | 99.9 99.8 | 100.0 99.9 | 100.0 100.0 | 88.9 99.2 |

EXAMPLES 27 TO 30

Various test catalysts as shown in the following Table 24 were prepared in the same manner as in Example 12. In the column for "Test catalyst" in Table 24, metal species of each complex oxide catalyst and their molar ratio, and the type of the additional metal oxide are indicated. The amount of the additional metal oxide supported, was 10 wt %. 6 ml of such a test catalyst was packed into a glass reactor having an inner diameter of 14 mm and heated to a predetermined temperature. Then, a reaction was conducted by supplying methanol and hydrogen chloride in a molar ratio of HCl/CH₃OH=1.3 at a space velocity SV=2,000 h⁻¹. The results are shown in Table 24. The reaction results after 500 hours in Table 24 are the results of the reaction conducted at a temperature of 200° C.

TABLE 24

| Exam- No. | Test catalyst Metal molar ratio | Kind of additives | Reaction result (mol %) (Upper column: CH₃OH conversion, Lower column: CH₃Cl selectivity) | | | | |
|---|---|---|---|---|---|---|---|
| | | | 200° C. | 250° C. | 300° C. | 350° C. | After 500 hrs |
| 27 | Zr/Al = 3 | Zinc oxide | 98.5 99.9 | 100.0 100.0 | 100.0 100.0 | 100.0 100.0 | 98.7 99.9 |
| 28 | Al/Zr = 3 | Zinc oxide | 97.3 99.8 | 100.0 99.9 | 100.0 100.0 | 100.0 100.0 | 97.5 99.8 |
| 29 | Ti/Al = 3 | Zinc oxide | 97.5 99.9 | 100.0 100.0 | 100.0 100.0 | 100.0 100.0 | 97.7 99.9 |
| 30 | Al/Ti = 3 | Zinc oxide | 96.2 99.6 | 100.0 99.9 | 100.0 100.0 | 100.0 100.0 | 96.3 99.5 |

EXAMPLE 31

Commercially available titania powder (specific surface area: 50 m²/g) was immersed in an aqueous zinc acetate solution and then dried at 110° C. for 15 hours. Then, the dried product was calcined at 500° C. for 4 hours so that zinc oxide was supported thereon in an amount of 10 wt %. The product was press-molded under a gauge pressure of 120 kg/cm², followed by pulverization and classification with sieves to obtain a catalyst having a particle size of from 10 to 20 mesh. The peak temperature for desorption of ammonia by the ammonia TPD method was 330° C. 6 cm³ of this catalyst was packed into a glass reactor having an inner diameter of 14 mm and heated to a predetermined temperature, and a reaction was conducted by supplying methanol and hydrogen chloride thereto in a molar ratio of HCl/CH₃OH=1.4 at a space velocity SV=2,200 h⁻¹. The results are shown in Table 25.

TABLE 25

| | Reaction temperature (°C.) | Conversion of methanol (mol %) | Selectivity for methyl chloride (mol %) |
|---|---|---|---|
| Initial activities | 200 | 96.5 | 99.8 |
| | 250 | 99.9 | 99.9 |
| | 300 | 100.0 | 100.0 |
| | 350 | 100.0 | 100.0 |
| After 200 hrs | 200 | 85.6 | 98.7 |

EXAMPLE 32

Commercially available zirconia powder (specific surface area: 80 m²/g) was immersed in an aqueous zinc nitrate solution and then dried at 120° C. for 12 hours. Then, the dried product was calcined at 500° C. for 3 hours so that zinc oxide was supported thereon in an amount of 9 wt %. The product was press-molded under a gauge pressure of 150 kg/cm², followed by pulverization and classification with sieves to obtain a test catalyst having a particle size of from 7 to 15 mesh. The peak temperature for liberation of ammonia by the ammonia TPD method was 230° C. 6 cm³ of this catalyst was packed into a glass reactor having an inner diameter of 14 mm and heated to a predetermined temperature. Then, a reaction was conducted by supplying methanol and hydrogen chloride thereto in a molar ratio of HCl/CH₃OH=1.3 at a space velocity SV=2,500 h⁻¹. The results are shown in Table 26.

TABLE 26

| | Reaction temperature (°C.) | Conversion of methanol (mol %) | Selectivity for methyl chloride (mol %) |
|---|---|---|---|
| Initial activities | 200 | 98.6 | 99.8 |
| | 250 | 99.9 | 100.0 |
| | 300 | 100.0 | 100.0 |

TABLE 26-continued

| | Reaction temperature (°C.) | Conversion of methanol (mol %) | Selectivity for methyl chloride (mol %) |
|---|---|---|---|
| | 350 | 100.0 | 100.0 |
| After 2,000 hrs | 200 | 98.6 | 99.7 |

EXAMPLE 33

Using zirconium oxynitrate as the zirconium source and aluminum nitrate as the aluinum source, a mixed aqueous solution was prepared so that the molar ratio of Zr/Al=2. This solution and 10% aqueous ammonia were gradually dropwise added to water under stirring to maintain pH=8, to form a coprecipitated gel. The gel was left to stand still for one day and then subjected to washing with water and filtration, and it was dried at 110° C. for 20 hours. The dried product was further pulverized and then calcined at 500° C. for 6 hours to obtain a complex oxide of $ZrO_2$—$Al_2O_3$. The obtained powder had a specific surface area of 95 m$^2$/g. This powder was immersed into an aqueous zinc acetate solution and then dried at 100° C. for 15 hours. Then, the dried product was calcined at 550° C. for 3 hours so that zinc oxide was supported thereon in an amount of 11 wt %. Then, the product was press-molded under a gauge pressure of 130 kg/cm$^2$, followed by pulverization and classification with sieves to obtain a test catalyst having a particle size of from 10 to 20 mesh. The peak temperature for desorption of ammonia by the ammonia TPD method was 200° C. 6 cm$^3$ of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.5 at a space velocity SV=1,600 h$^{-1}$. The results are shown in Table 27.

TABLE 27

| | Reaction temperature (°C.) | Conversion of methanol (mol %) | Selectivity for methyl chloride (mol %) |
|---|---|---|---|
| Initial activities | 200 | 98.7 | 99.9 |
| | 250 | 100.0 | 100.0 |
| | 300 | 100.0 | 100.0 |
| | 350 | 100.0 | 100.0 |
| After 2,000 hrs | 200 | 98.8 | 99.8 |

EXAMPLE 34

Using zirconium oxychloride as the zirconium source and titanium isopropoxide as the titanium source, a mixed aqueous solution was prepared so that the molar ratio of Zr/Ti=1.5. This solution and 10% aqueous ammonia were gradually dropwise added to water under stirring to maintain pH=7, to form a coprecipitated gel. The gel was left to stand still for one day and then subjected to washing with water and filtration, and it was dried at 100° C. for220 hours. The dried product was further pulverized and then calcined at 550° C. for 5 hours to obtain a complex oxide of $ZrO_2$—$TiO_2$. The obtained powder had a specific surface area of 96 m$^2$/g. This powder was immersed into an aqueous zinc nitrate solution and then dried at 110° C. for 12 hours. Then, the dried product was calcined at 500° C. for 4 hours so that zinc oxide was supported thereon in an amount of 10 wt %. Then, the product was press-molded under a gauge pressure of 140 kg/cm$^2$, followed by pulverization and classification with sieves to obtain a test catalyst having a particle size of from 7 to 15 mesh. The peak temperature for desorption of ammonia by the ammonia TPD method was 200° C. 6 cm$^3$ of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.4 at a space velocity SV=2,300 h$^{-1}$. The results are shown in Table 28.

TABLE 28

| | Reaction temperature (°C.) | Conversion of methanol (mol %) | Selectivity for methyl chloride (mol %) |
|---|---|---|---|
| Initial activities | 200 | 98.9 | 99.9 |
| | 250 | 100.0 | 100.0 |
| | 300 | 100.0 | 100.0 |
| | 350 | 100.0 | 100.0 |
| After 2,000 hrs | 200 | 98.9 | 99.8 |

EXAMPLE 35

Using titanium chloride as the titanium source and aluminum nitrate as the aluminum source, a mixed aqueous solution was prepared so that the molar ratio of Al/Ti=1 and adjusted to pH=0.9 with hydrochloric acid. This solution and 10% aqueous ammonia were gradually dropwise added to water under stirring to maintain pH=8, to form a coprecipitated gel. The gel was left to stand still for one day and then subjected to washing with water and filtration, and it was dried at 100° C. for 20 hours. The dried product was further pulverized and then calcined at 500° C. for 6 hours to obtain a complex oxide of $Al_2O_3$—$TiO_2$. The obtained powder had a specific surface area of 85 m$^2$/g. This powder was immersed into an aqueous zinc acetate solution and then dried at 110° C. for 10 hours. Then, the dried product was calcined at 500° C. for 3 hours so that zinc oxide was supported thereon in an amount of 9 wt %. Then, the product was press-molded under a gauge pressure of 130 kg/cm$^2$, followed by pulverization and classification with sieves to obtain a test catalyst having a particle size of from 10 to 20 mesh. The peak temperature for desorption of ammonia by the ammonia TPD method was 200° C. 6 cm$^3$ of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.5 at a space velocity SV=2,100 h$^{-1}$. The results are shown in Table 29.

TABLE 29

| | Reaction temperature (°C.) | Conversion of methanol (mol %) | Selectivity for methyl chloride (mol %) |
|---|---|---|---|
| Initial activities | 200 | 98.8 | 99.8 |
| | 250 | 100.0 | 100.0 |
| | 300 | 100.0 | 100.0 |
| | 350 | 100.0 | 100.0 |
| After 1,000 hrs | 200 | 98.7 | 99.7 |

EXAMPLE 36

Using zinc nitrate as the zinc source and zirconium oxychloride as the zirconium source, a mixed aqueous solution was prepared so that the molar ratio of Zn/Zr=0.17. This solution and 10% aqueous ammonia were gradually dropwise added to water under stirring to maintain pH=8, to form a coprecipitated gel. The gel was left to stand still for one day and then subjected to washing with water and filtration, and it was dried at 100° C. for 24 hours. The dried product was further pulverized and then calcined at 500° C. for 8 hours to obtain a complex oxide of $ZnO-ZrO_2$. The obtained powder had a specific surface area of 69 m$^2$/g. Then, the power was press-molded under a gauge pressure of 140 kg/cm$^2$, followed by pulverization and classification with sieves to obtain a test catalyst having a particle size of from 10 to 20 mesh. The peak temperature for desorption of ammonia by the ammonia TPD method was 250° C. 6 cm$^3$ of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.4 at a space velocity SV=2,200 h$^{-1}$. The results are shown in Table 30.

TABLE 30

| | Reaction temperature (°C.) | Conversion of methanol (mol %) | Selectivity for methyl chloride (mol %) |
|---|---|---|---|
| Initial activities | 200 | 98.8 | 99.8 |
| | 250 | 100.0 | 100.0 |
| | 300 | 100.0 | 100.0 |
| | 350 | 100.0 | 100.0 |
| After 500 hrs | 200 | 98.8 | 99.7 |

EXAMPLE 37

Using zinc nitrate as the zinc source and titanium chloride as the titanium source, a mixed aqueous solution was prepared so that the molar ratio of Zn/Ti=0.11. The mixed aqueous solution and 10% aqueous ammonia were gradually dropwise added to water under stirring to maintain pH=8, to form a coprecipitated gel. The gel was left to stand still for one day and then subjected to washing with water and filtration, and it was dried at 120° C. for 20 hours. The dried product was further pulverized and then calcined at 500° C. for 6 hours to obtain a complex oxide of $ZnO-TiO_2$. The obtained powder had a specific surface area of 88 m$^2$/g. Then, the power was press-molded under a gauge pressure of 130 kg/cm$^2$, followed by pulverization and classification with sieves to obtain a test catalyst having a particle size of from 10 to 20 mesh. The peak temperature for desorption of ammonia by the ammonia TPD method was 250° C. 6 cm$^3$ of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.5 at a space velocity SV=1,800 h$^{-1}$. The results are shown in Table 31.

TABLE 31

| | Reaction temperature (°C.) | Conversion of methanol (mol %) | Selectivity for methyl chloride (mol %) |
|---|---|---|---|
| Initial activities | 200 | 98.5 | 99.8 |
| | 250 | 100.0 | 100.0 |
| | 300 | 100.0 | 100.0 |
| | 350 | 100.0 | 100.0 |
| After 500 hrs | 200 | 98.5 | 99.6 |

EXAMPLE 38

Using zinc nitrate as the zinc source, zirconium oxynitrate as the zirconium source and aluminum nitrate as the aluminum source, a mixed aqueous solution was prepared so that the molar ratio of Zn/Zr/Al=0.3/1/1. The mixed aqueous solution and 10% aqueous ammonia were gradually dropwise added to water under stirring to maintain pH=8, to form a coprecipitated gel. The gel was left to stand still for one day and then subjected to washing with water and filtration, and it was dried at 110° C. for 20 hours. The dried product was further pulverized and then calcined at 550° C. for 6 hours to obtain a complex oxide of $ZnO-ZrO_2-Al_2O_3$. The obtained powder had a specific surface area of 62 m$^2$/g. Then, the power was press-molded under a gauge pressure of 140 kg/cm$^2$, followed by pulverization and classification with sieves to obtain a test catalyst having a particle size of from 10 to 20 mesh. The peak temperature for desorption of ammonia by the ammonia TPD method was 200° C. 6 cm$^3$ of this catalyst was packed into a glass reactor having an inner diameter of 14 mm and heated to a predetermined temperature. Then, a reaction was conducted by supplying methanol and hydrogen chloride thereto in a molar ratio of HCl/CH$_3$OH=1.6 at a space velocity SV=2,300 h$^{-1}$. The results are shown in Table 32.

TABLE 32

| | Reaction temperature (°C.) | Conversion of methanol (mol %) | Selectivity for methyl chloride (mol %) |
|---|---|---|---|
| Initial activities | 200 | 99.0 | 99.9 |
| | 250 | 100.0 | 100.0 |
| | 300 | 100.0 | 100.0 |
| | 350 | 100.0 | 100.0 |
| After 1,000 hrs | 200 | 99.1 | 99.9 |

EXAMPLE 39

Using zinc acetate as the zinc source, zirconium oxychloride as the zirconium source and titanium isopropoxide as the titanium source, a mixed aqueous solution was prepared so that the molar ratio of Zn/Zr/Ti=0.25/1/1 and adjusted to pH=1 with HNO$_3$. This solution and 10% aqueous ammonia were gradually dropwise added to water under stirring to maintain pH=8, to form a coprecipitated gel. The gel was left to stand still for one day and then subjected to washing with water and filtration, and it was dried at 100° C. for 24 hours. The dried product was further pulverized and then calcined at 500° C. for 6 hours to obtain a complex oxide of $ZnO-ZrO_2-TiO_2$. The obtained powder had a specific surface area of 70 m$^2$/g. Then, the powder was press-molded under a gauge pressure of 120 kg/cm$^2$, followed by pulverization and classification with sieves to obtain a test catalyst having a particle size of from 7 to 15 mesh. The peak temperature for desorption of ammonia by the ammonia TPD method was 200° C. 6 cm³ of this catalyst was packed into a glass reactor having an inner diameter of 14 mm and heated to a predetermined temperature. Then, a reaction was conducted by supplying methanol and hydrogen chloride thereto in a molar ratio of HCl/CH₃OH = 1.4 at a space velocity SV = 2,300 h⁻¹. The results are shown in Table 33.

TABLE 33

|  | Reaction temperature (°C.) | Conversion of methanol (mol %) | Selectivity for methyl chloride (mol %) |
|---|---|---|---|
| Initial activities | 200 | 99.1 | 99.9 |
|  | 250 | 100.0 | 100.0 |
|  | 300 | 100.0 | 100.0 |
|  | 350 | 100.0 | 100.0 |
| After 1,000 hrs | 200 | 99.2 | 99.9 |

COMPARATIVE EXAMPLE 3

Commercially available γ-alumina powder (specific surface area: 140 m²/g) was calcined at 500° C. for 4 hours in an electric furnace. This powder was press-molded under a gauge pressure of 150 kg/cm², followed by pulverization and classification with sieves to obtain a test catalyst having a particle size of from 10 to 20 mesh. The peak temperature for desorption of ammonia by the ammonia TPD method was 380° C. 6 cm³ of this catalyst was packed into a glass reactor having an inner diameter of 14 mm and heated to a predetermined temperature. Then, a reaction was conducted by supplying methanol and hydrogen chloride thereto in a molar ratio of HCl/CH₃OH = 1.4 at a space velocity SV = 2,000 h⁻¹. The results are shown in Table 34.

TABLE 34

|  | Reaction temperature (°C.) | Conversion of methanol (mol %) | Selectivity for methyl chloride (mol %) |
|---|---|---|---|
| Initial activities | 200 | 15.8 | 98.3 |
|  | 250 | 77.5 | 99.1 |
|  | 300 | 96.3 | 99.8 |
|  | 350 | 99.8 | 99.9 |
| After 200 hrs | 200 | 10.3 | 97.5 |

EXAMPLE 40

Commercially available zirconia powder (specific surface area: 100 m²/g) was calcined at 500° C. for 3 hours in an electric furnace. This powder was press-molded under a gauge pressure of 120 kg/cm², followed by pulverization and classification with sieves to obtain a test catalyst having a particle size of from 10 to 20 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF = 100 ppm) thereto in a molar ratio of HCl/CH₃OH = 1.4/1 at a space velocity SV = 2,200 h⁻¹. The results are shown in Table 35.

TABLE 35

|  |  | Reaction temperature (°C.) | Conversion of methanol (mol %) | Selectivity for methyl chloride (mol %) |
|---|---|---|---|---|
| Example 40 | Initial activities | 200 | 10.1 | 93.5 |
|  |  | 250 | 15.8 | 94.3 |
|  |  | 300 | 57.2 | 97.5 |
|  |  | 350 | 84.2 | 98.5 |
|  | After 1,000 hrs | 250 | 15.7 | 94.3 |
| Example 41 | Initial activities | 200 | 98.5 | 99.8 |
|  |  | 250 | 100.0 | 100.0 |
|  |  | 300 | 100.0 | 100.0 |
|  |  | 350 | 100.0 | 100.0 |
|  | After 2,000 hrs | 200 | 98.6 | 99.8 |

EXAMPLE 41

Commercially available zirconia powder (specific surface area: 80 m²/g) was immersed in an aqueous zinc nitrate solution and then dried at 120° C. for 10 hours. Then, the dried powder was clacined at 500° C. for 4 hours so that zinc oxide was supported thereon in an amount of 10 wt %. This product was press-molded under a gauge pressure of 150 kg/cm², followed by pulverization and classification with sieves to obtain a test catalyst having a particle size of from 7 to 15 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF = 200 ppm) thereto in a molar ratio of HCl/CH₃OH = 1.3/1 at a space velocity SV = 2,500 h⁻¹. The results are shown in Table 35.

EXAMPLE 42

Commercially available zirconia powder (specific surface area: 80 m²/g) was immersed in an aqueous chromium acetate solution and then dried at 120° C. for 6 hours. Then, the dried powder was clacined at 450° C. for 4 hours so that chromium oxide was supported thereon in an amount of 9 wt %. The product was press-molded under a gauge pressure of 130 kg/cm², followed by pulverization and classification with sieves to obtain a test catalyst having a particle size of from 10 to 20 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF = 100 ppm) thereto in a molar ratio of HCl/CH₃OH = 1.4/1 at a space velocity SV = 2,200 h⁻¹. The results are shown in Table 36.

TABLE 36

|  |  | Reaction temperature (°C.) | Conversion of methanol (mol %) | Selectivity for methyl chloride (mol %) |
|---|---|---|---|---|
| Example 42 | Initial activities | 200 | 95.3 | 99.3 |
|  |  | 250 | 98.2 | 99.7 |
|  |  | 300 | 99.9 | 99.9 |
|  |  | 350 | 100.0 | 99.9 |
| Example 43 | Initial activities | 200 | 15.3 | 98.0 |
|  |  | 250 | 90.3 | 98.8 |
|  |  | 300 | 99.2 | 99.9 |
|  |  | 350 | 100.0 | 99.8 |
| Example 44 | Initial activities | 200 | 20.3 | 98.0 |
|  |  | 250 | 98.1 | 99.6 |
|  |  | 300 | 100.0 | 100.0 |

TABLE 36-continued

| Reaction temperature (°C.) | Conversion of methanol (mol %) | Selectivity for methyl chloride (mol %) |
|---|---|---|
| 350 | 100.0 | 99.9 |

EXAMPLE 43

Commercially available zirconia powder (specific surface area: 100 m$^2$/g) was immersed in an aqueous copper acetate solution and then dried at 110° C. for 9 hours. The dried powder was clacined at 500° C. for 3 hours so that copper oxide was supported thereon in an amount of 11 wt %. The product was press-molded under a gauge pressure of 140 kg/cm$^2$, followed by pulverization and classification with sieves to obtain a test catalyst having a particle size of from 7 to 15 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF=150 ppm) thereto in a molar ratio of HCl/CH$_3$OH=1.3/1 at a space velocity SV=2,500 h$^{-1}$. The results are shown in Table 36.

EXAMPLE 44

Commercially available zirconia powder (specific surface area: 100 m$^2$/g) was immersed in an aqueous manganese nitrate solution and then dried at 100° C. for 12 hours. The dried powder was clacined at 550° C. for 4 hours so that manganese oxide was supported thereon in an amount of 10 wt %. The product was press-molded under a gauge pressure of 130 kg/cm$^2$, followed by pulverization and classification with sieves to obtain a test catalyst having a particle size of from 10 to 20 mesh. 6 ml of this catalyst was packed into an Inconel reactor having an inner diameter of 14 mm and heated to a predetermined temperature. Then, a reaction was conducted by supplying methanol and hydrogen chloride thereto in a molar ratio of HCl/CH$_3$OH=1.4/1 at a space velocity SV=2,300 h$^{-1}$. The results are shown in Table 36.

EXAMPLE 45

Commercially available zirconia powder (specific surface area: 80 m$^2$/g) was immersed in an aqueous cobalt nitrate solution and then dried at 110° C. for 8 hours. Then, the dried product was calcined at 500° C. for 4 hours so that cobalt oxide was supported thereon in an amount of 9 wt %. The product was press-molded under a gauge pressure of 120 kg/cm$^2$, followed by pulverization and classification with sieves to obtain a test catalyst having a particle size of from 10 to 20 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF=200 ppm) thereto in a molar ratio of HCl/CH$_3$OH=1.3/1 at a space velocity SV=2,500 h$^{-1}$. The results are shown in Table 37.

TABLE 37

| | | Reaction temperature (°C.) | Conversion of methanol (mol %) | Selectivity for methyl chloride (mol %) |
|---|---|---|---|---|
| Example | Initial | 200 | 18.2 | 98.0 |

TABLE 37-continued

| | | Reaction temperature (°C.) | Conversion of methanol (mol %) | Selectivity for methyl chloride (mol %) |
|---|---|---|---|---|
| 45 | activities | 250 | 95.8 | 99.2 |
| | | 300 | 99.5 | 99.4 |
| | | 350 | 100.0 | 100.0 |
| Example | Initial | 200 | 70.2 | 99.0 |
| 46 | activities | 250 | 98.3 | 99.7 |
| | | 300 | 100.0 | 99.9 |
| | | 350 | 100.0 | 99.9 |
| Example | Initial | 200 | 85.3 | 98.9 |
| 47 | activities | 250 | 99.9 | 99.8 |
| | | 300 | 100.0 | 100.0 |
| | | 350 | 100.0 | 100.0 |

EXAMPLE 46

Commercially available zirconia powder (specific surface area: 100 m$^2$/g) was immersed in an aqueous iron nitrate solution and then dried at 110° C. for 12 hours. Then, the dried product was calcined at 600° C. for 2 hours so that iron oxide was supported thereon in an amount of 10 wt %. The product was press-molded under a gauge pressure of 150 kg/cm$^2$, followed by pulverization and classification with sieves to obtain a test catalyst having a particle size of from 7 to 15 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF=200 ppm) thereto in a molar ratio of HCl/CH$_3$OH=1.5/1 at a space velocity SV=2,500 h$^{-1}$. The results are shown in Table 37.

EXAMPLE 47

Commercially available zirconia powder (specific surface area: 100 m$^2$/g) was immersed in an aqueous nickel acetate solution and then dried at 120° C. for 6 hours. Then, the dried product was calcined at 500° C. for 3 hours so that nickel oxide was supported thereon in an amount of 11 wt %. The product was press-molded under a gauge pressure of 120 kg/cm$^2$, followed by pulverization and classification with sieves to obtain a test catalyst having a particle size of from 10 to 20 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF=100 ppm) thereto in a molar ratio of HCl/CH$_3$OH=1.4/1 at a space velocity SV=2,300 h$^{-1}$. The results are shown in Table 37.

EXAMPLE 48

Using zinc nitrate as the zinc source and zirconium oxynitrate as the zirconium source, a mixed aqueous solution was prepared so that the molar ratio of Zn/Zr=0.1/1. This mixed aqueous solution and 10% aqueous ammonia were gradually dropwise added to water under stirring to maintain pH=8, to form a coprecipitated gel. The coprecipitated gel was left to stand still for one day and then subjected to washing with water and filtration, and it was dried at 110° C. for 20 hours. The dried product was further pulverized and calcined at 500° C. for 10 hours to obtain a complex oxide catalyst of ZnO—ZrO$_2$. The complex oxide catalyst had a ZnO content of 6.2 wt % and a specific surface area of 95 m$^2$/g. Then, the complex oxide catalyst was press-molded under a gauge pressure of 150 kg/cm², followed by pulverization and classification with sieves to obtain a test catalyst having a particle size of from 10 to 20 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF=150 ppm) thereto in a molar ratio of $HCl/CH_3OH=1.5/1$ at a space velocity $SV=2,000$ $h^{-1}$. The results are shown in Table 38.

TABLE 38

| | | Reaction temperature (°C.) | Conversion of methanol (mol %) | Selectivity for methyl chloride (mol %) |
|---|---|---|---|---|
| Example 48 | Initial activities | 200 | 99.8 | 99.9 |
| | | 250 | 100.0 | 100.0 |
| | | 300 | 100.0 | 100.0 |
| | | 350 | 100.0 | 100.0 |
| Example 49 | Initial activities | 200 | 99.8 | 99.9 |
| | | 250 | 100.0 | 100.0 |
| | | 300 | 100.0 | 100.0 |
| | | 350 | 100.0 | 100.0 |
| Example 50 | Initial activities | 200 | 95.5 | 99.5 |
| | | 250 | 98.5 | 99.7 |
| | | 300 | 100.0 | 99.9 |
| | | 350 | 100.0 | 99.9 |

EXAMPLE 49

Using zinc chloride as the zinc source and zirconium oxychloride as the zirconium source, a mixed aqueous solution was prepared so that the molar ratio of $Zn/Zr=0.01/1$. This mixed aqueous solution and 10% aqueous ammonia were gradually dropwise added to water under stirring to maintain pH=8, to form a co-precipitated gel. The coprecipitated gel was left to stand still for one day and then subjected to washing with water and filtration, and it was dried at 120° C. for 15 hours. The dried product was further pulverized and calcined at 550° C. for 8 hours to obtain a complex oxide catalyst of $ZnO—ZrO_2$. The complex oxide catalyst had a ZnO content of 0.6 wt % and a specific surface area of 90 m²/g. Then, the complex oxide catalyst was press-molded under a gauge pressure of 140 kg/cm², followed by pulverization and classification with sieves to obtain a test catalyst having a particle size of from 7 to 15 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF=100 ppm) thereto in a molar ratio of $HCl/CH_3OH=15/1$ at a space velocity $SV=1,800$ $h^{-1}$. The results are shown in Table 38.

EXAMPLE 50

Using chromium nitrate as the chromium source and zirconium oxychloride as the zirconium source, a mixed aqueous solution was prepared so that the molar ratio of $Cr/Zr=0.1/1$. This mixed aqueous solution and 10% aqueous ammonia were gradually dropwise added to water under stirring to maintain pH=8, to form a co-precipitated gel. The coprecipitated gel was left to stand still for one day and then subjected to washing with water and filtration, and it was dried at 100° C. for 20 hours. The dried product was further pulverized and calcined at 500° C. for 8 hours to obtain a complex oxide catalyst of $Cr_2O_3—ZrO_2$. The complex oxide catalyst had a $Cr_2O_3$ content of 11.0 wt % and a specific surface area of 85 m²/g. Then, the composite catalyst was press-molded under a gauge pressure of 150 kg/cm², followed by pulverization and classification with sieves to obtain a test catalyst having a particle size of from 10 to 20 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF=200 ppm) thereto in a molar ratio of $HCl/CH_3OH=1.6/1$ at a space velocity $SV=2,200$ $h^{-1}$. The results are shown in Table 38.

COMPARATIVE EXAMPLE 4

Commercially available γ-alumina powder (specific surface area: 140 m²/g) was calcined at 500° C. for 4 hours in an electric furnace. This powder was press-molded under a gauge pressure of 120 kg/cm², followed by pulverization and classification with sieves to obtain a test catalyst having a particle size of from 10 to 20 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF=200 ppm) thereto in a molar ratio of $HCl/CH_3OH=1.3/1$ at a space velocity $SV=2,000$ $h^{-1}$. The results are shown in Table 39.

TABLE 39

| | | Reaction temperature (°C.) | Conversion of methanol (mol %) | Selectivity for methyl chloride (mol %) |
|---|---|---|---|---|
| Comparative Example 4 | Initial activities | 200 | 7.1 | 93.3 |
| | | 250 | 13.2 | 94.1 |
| | | 300 | 50.5 | 97.3 |
| | | 350 | 78.3 | 98.3 |
| | After 1,000 hrs | 250 | 6.5 | 92.5 |
| Comparative Example 5 | Initial activities | 200 | 57.3 | 98.3 |
| | | 250 | 79.8 | 98.5 |
| | | 300 | 88.2 | 98.9 |
| | | 350 | 90.5 | 99.3 |
| | After 1,000 hrs | 200 | 20.1 | 93.7 |

COMPARATIVE EXAMPLE 5

Commercially available γ-alumina powder (specific surface area: 140 m²/g) was immersed in an aqueous zinc nitrate solution and then dried at 120° C. for 10 hours. Then, the dried product was calcined at 500° C. for 4 hours so that zinc oxide was supported thereon in an amount of 10 wt %. The product was press-molded under a gauge pressure of 150 kg/cm², followed by pulverization and classification with sieves to obtain a test catalyst having a particle size of from 7 to 15 mesh. 6 ml of this catalyst was packed into an Inconel reactor having an inner diameter of 14 mm and heated to a predetermined temperature. Then, a reaction was conducted by supplying methanol and hydrogen chloride containing hydrogen fluoride (HF=200 ppm) thereto in a molar ratio of $HCl/CH_3OH=1.3/1$ at a space velocity $SV=2,500$ $h^{-1}$. The results are shown in Table 39.

We claim:

1. A method for producing methyl chloride, which comprises reacting methanol and hydrogen chloride in a gas phase in the presence of a catalyst, wherein a zirconium oxide catalyst or a complex oxide catalyst comprising at least two oxides of metals selected from the group consisting of Zr, Ti and Al, is used as the catalyst.

2. The method for producing methyl chloride according to claim 1, wherein the zirconium oxide catalyst or the complex oxide catalyst is used which has at least one oxide of metal selected from the group consisting of zinc, copper, manganese, cobalt, chromium, iron and nickel incorporated therein.

3. The method for producing methyl chloride according to claim 1, wherein the zirconium oxide is an oxide of tetravalent zirconium.

4. The method for producing methyl chloride according to claim 1, wherein the oxide of Ti is an oxide of tetravalent titanium.

5. The method for producing methyl chloride according to claim 1, wherein the oxide of Al is an oxide of trivalent aluminum.

6. The method for producing methyl chloride according to claim 1, wherein the hydrogen chloride contains from 10 ppm to 10 wt % of hydrogen fluoride.

* * * * *